United States Patent
Colletti

(10) Patent No.: US 9,733,195 B2
(45) Date of Patent: Aug. 15, 2017

(54) SYSTEM AND METHOD FOR INSPECTING TURBINE BLADES

(71) Applicant: General Electric Company, Schenectady, NY (US)

(72) Inventor: Andrew Joseph Colletti, Greenville, SC (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/974,210

(22) Filed: Dec. 18, 2015

(65) Prior Publication Data

US 2017/0176342 A1    Jun. 22, 2017

(51) Int. Cl.
| | |
|---|---|
| *G01N 21/00* | (2006.01) |
| *G01N 21/88* | (2006.01) |
| *G01M 15/14* | (2006.01) |
| *F01D 5/00* | (2006.01) |
| *F01D 21/00* | (2006.01) |

(52) U.S. Cl.
CPC ......... *G01N 21/8806* (2013.01); *F01D 5/005* (2013.01); *F01D 21/003* (2013.01); *G01M 15/14* (2013.01); *F05D 2220/32* (2013.01); *F05D 2240/24* (2013.01); *F05D 2240/30* (2013.01); *G01N 2201/061* (2013.01); *G01N 2201/06113* (2013.01); *G01N 2201/101* (2013.01)

(58) Field of Classification Search
CPC ............... G01N 21/954; G01N 29/262; G01N 2291/2693; G01N 25/72; G01N 17/00; G01N 2291/02836; G01N 2291/02881; G01N 2291/044; G01N 2291/106; G01N 29/043; G01N 29/069; G01N 29/07; G01N 29/4436

See application file for complete search history.

(56) References Cited

U.S. PATENT DOCUMENTS

| | | | |
|---|---|---|---|
| 4,501,095 A * | 2/1985 | Drinkuth | B24B 19/14 29/889.2 |
| 6,341,936 B1 | 1/2002 | Cowie et al. | |
| 6,912,446 B2 | 6/2005 | Wang et al. | |
| 2005/0171733 A1 | 8/2005 | Hough | |
| 2007/0132840 A1 * | 6/2007 | Konomura | G01N 21/954 348/65 |
| 2009/0185177 A1 | 7/2009 | Manfred | |

(Continued)

FOREIGN PATENT DOCUMENTS

EP    1777493 A2    4/2007

OTHER PUBLICATIONS

EP Search Report regarding application No. 16203161.1-1504 dated May 12, 2017.

*Primary Examiner* — Michael P Stafira
(74) *Attorney, Agent, or Firm* — Mark E. Henderson; Ernest G. Cusick; Frank A. Landgraff

(57) ABSTRACT

A system for inspecting surfaces of rotor blades for a surface characteristic. The system may include an assembly having a movable arm and, mounted on the movable arm, a scanner. A row of rotor blades may be positioned near the assembly for inspection. The row of rotor blades may include a plurality of the rotor blades circumferentially spaced about a center axis. The row of rotor blades and the assembly may be moved relative to the other so as to index the row of rotor blades relative to the assembly.

19 Claims, 7 Drawing Sheets

(56) References Cited

U.S. PATENT DOCUMENTS

| | | | |
|---|---|---|---|
| 2011/0138873 A1* | 6/2011 | Razi | B21J 15/02 72/453.01 |
| 2012/0266680 A1* | 10/2012 | Boyer | G01B 11/161 73/655 |
| 2013/0335549 A1* | 12/2013 | Hatcher, Jr. | G02B 23/2484 348/82 |
| 2015/0176413 A1 | 6/2015 | Weber et al. | |

* cited by examiner

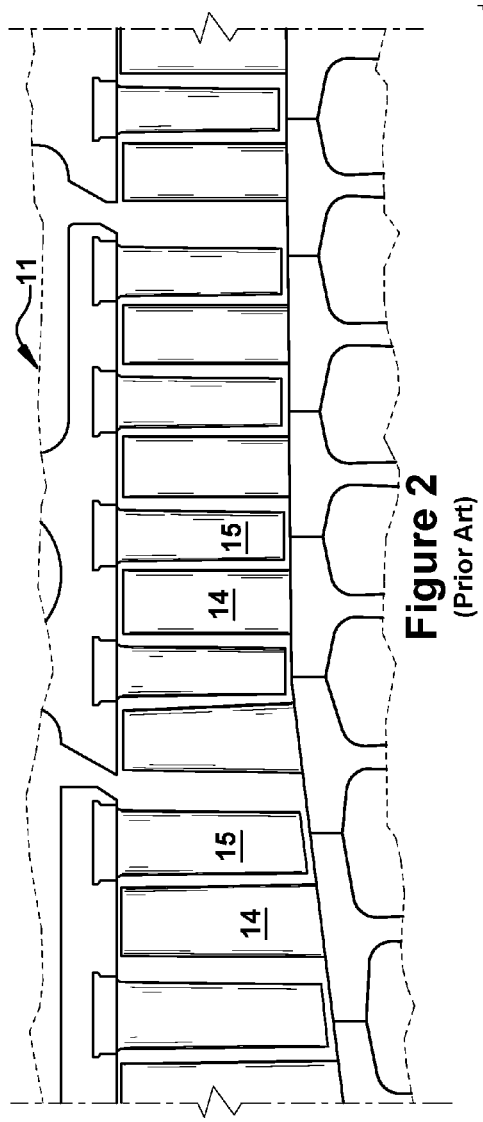
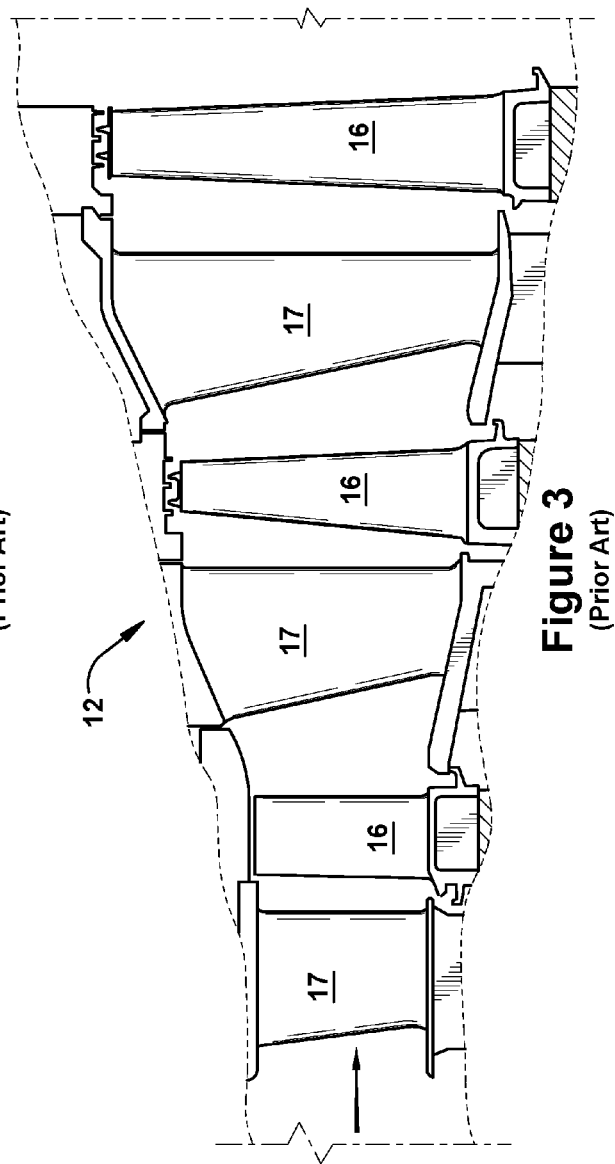

SYSTEM AND METHOD FOR INSPECTING TURBINE BLADES

BACKGROUND OF THE INVENTION

The present application relates to systems and methods for performing an inspection of turbine rotor blades. More particularly, but not by way of limitation, the present application relates to a technique for inspecting turbine rotor blade surfaces for any irregularities, defects, or other types of flaws on the blade surface.

It will be appreciated that combustion or gas turbine engines ("gas turbines") include a compressor, combustor, and turbine. The compressor and turbine sections generally include rows of blades that are axially stacked in stages. Each stage includes a row of circumferentially-spaced stator blades, which are fixed, and a row of the rotor blades, which rotate about a central turbine axis. In operation, generally, the compressor rotor blades rotate about the central axis, and, acting in concert with the stator blades, compress a flow of air. The supply of compressed air then is used in the combustor to combust a supply of fuel. The resulting flow of hot expanding gases from the combustion, i.e., the working fluid, is expanded through the turbine section of the engine. The flow of working fluid through the turbine induces the rotor blades to rotate. The rotor blades are connected to a central shaft such that the rotation of the rotor blades rotates the shaft. The shaft may further be connection to the rotor blades within the compressor. The energy contained in the fuel, thus, may be converted into the mechanical energy of the rotating shaft, which, for example, may be used to rotate the rotor blades of the compressor, such that the supply of compressed air needed for combustion is produced, as well as, the coils of a generator so to generate electrical power.

In the gas turbine industry, advancing technology is required to meet necessary power output requirements in a cost-effective manner. During operation of a gas turbine, the blades of both the compressor and turbine are subject to damage from a variety of sources, including creep from long-term exposure to heat, cracks and stress from fatigue, and nicking in the blade surface from foreign particles of dust and other materials present in the air flowing through the gas turbine. Such incidents of damage introduce deformations in the surface of blades, concomitantly reducing the overall efficiency and increasing the fuel consumption needed for the turbine system to operate at a desired output.

To address the issue of blade surface damage, the turbine engine is occasionally removed from operation, disassembled, and inspected to ensure that the blades are properly functioning. A major component of this inspection typically includes a visual inventory of the surfaces of each blade, looking for signs of damage, including deformations, tears, rips, holes, cracks, and any other defects. This inspection is performed manually for each surface of each blade, introducing a high amount of error and variability in the process of maintaining blades. Moreover, for the inspection process to yield meaningful results, it requires an enormous investment in both time and labor resources. Overall, the arduous conventional inspection process, combined with the probability of errors during such inspections, collectively contribute to more frequent and longer engine downtimes and an increased risk of failure events. As will be appreciated, these issues add significant cost to the operation and maintenance of gas turbines. Systems and methods that improve aspects of the inspection process relating to gas turbine blades would be demanded in the marketplace.

BRIEF DESCRIPTION OF THE INVENTION

The present application thus describes a system for inspecting surfaces of rotor blades for a surface characteristic. The system may include an assembly having a movable arm and, mounted on the movable arm, a scanner. A row of rotor blades may be positioned near the assembly for inspection. The row of rotor blades may include a plurality of the rotor blades circumferentially spaced about a center axis. The row of rotor blades and the assembly may be moved relative to the other so as to index the row of rotor blades relative to the assembly.

The present application further describes a method for inspecting surfaces of rotor blades that are mounted on a rotor disc. The method may include: desirably positioning an assembly that includes a scanner mounted on a movable arm near the rotor blades; rotating the rotor disc so to index the rotor blades the assembly; controllably moving the scanner via the moveable arm between an indexing position and a scanning position; and scanning the surfaces of the rotor blades when the scanner is in the indexing position.

These and other features of the present application will become apparent upon review of the following detailed description of the preferred embodiments when taken in conjunction with the drawings and the appended claims.

BRIEF DESCRIPTION OF THE DRAWINGS

These and other features of this invention will be more completely understood and appreciated by careful study of the following more detailed description of exemplary embodiments of the invention taken in conjunction with the accompanying drawings, in which:

FIG. 2 is a sectional view of the compressor section of the gas turbine of FIG. 1;

FIG. 3 is a sectional view of the turbine section of the gas turbine of FIG. 1;

DETAILED DESCRIPTION OF THE INVENTION

Figure 1:
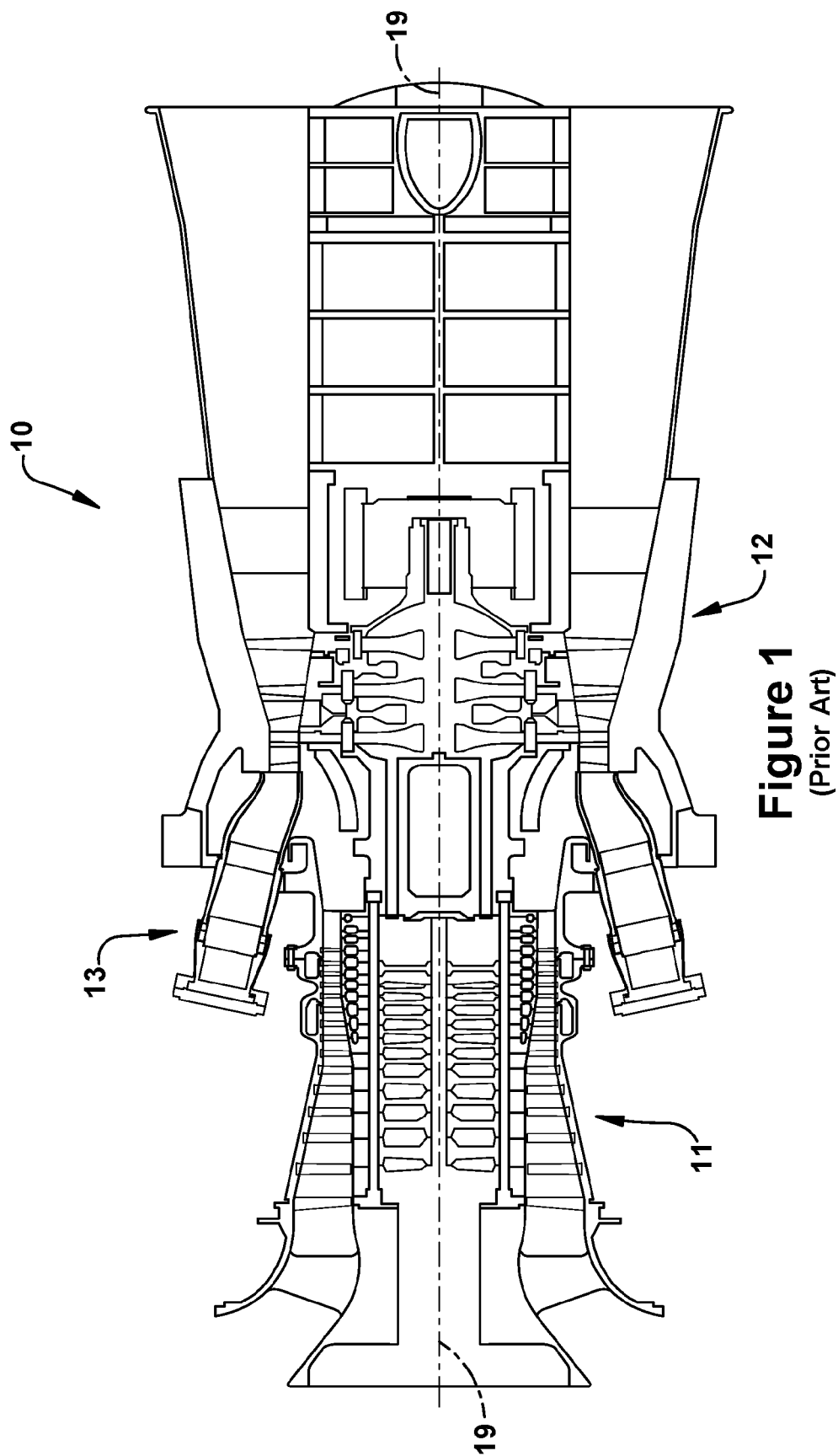
FIG. 1 is a schematic representation of an exemplary gas turbine having blades which may be inspected according to embodiments of the present application.

Aspects and advantages of the invention are set forth below in the following description, or may be obvious from the description, or may be learned through practice of the invention. Reference will now be made in detail to present embodiments of the invention, one or more examples of which are illustrated in the accompanying drawings. The detailed description uses numerical designations to refer to features in the drawings. Like or similar designations in the drawings and description may be used to refer to like or similar parts of embodiments of the invention. As will be appreciated, each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents. It is to be understood that the ranges and limits mentioned herein include all sub-ranges located within the prescribed limits, inclusive of the limits themselves unless otherwise stated. Additionally, certain terms have been selected to describe the present invention and its component subsystems and parts. To the extent possible, these terms have been chosen based on the terminology common to the technology field. Still, it will be appreciate that such terms often are subject to differing interpretations. For example, what may be referred to herein as a single component, may be referenced elsewhere as consisting of multiple components, or, what may be referenced herein as including multiple components, may be referred to elsewhere as being a single component. In understanding the scope of the present invention, attention should not only be paid to the particular terminology used, but also to the accompanying description and context, as well as the structure, configuration, function, and/or usage of the component being referenced and described, including the manner in which the term relates to the several figures, as well as, of course, the precise usage of the terminology in the appended claims. Further, while the following examples are presented in relation to a certain type of gas turbine or turbine engine, the technology of the present invention also may be applicable to other types of turbine engines as would the understood by a person of ordinary skill in the relevant technological arts.

Given the nature of gas turbine operation, several descriptive terms may be used throughout this application so to explain the functioning of the engine and/or the several sub-systems or components included therewithin, and it may prove beneficial to define these terms at the onset of this section. Accordingly, these terms and their definitions, unless stated otherwise, are as follows. The terms "forward" and "aft" or "aftward", without further specificity, refer to directions relative to the orientation of the gas turbine. That is, "forward" refers to the forward or compressor end of the engine, and "aft" or "aftward" refers to the aft or turbine end of the engine. It will be appreciated that each of these terms may be used to indicate movement or relative position within the engine. The terms "downstream" and "upstream" are used to indicate position within a specified conduit relative to the general direction of flow moving through it. (It will be appreciated that these terms reference a direction relative to an expected flow during normal operation, which should be plainly apparent to anyone of ordinary skill in the art.) The term "downstream" refers to the direction in which the fluid is flowing through the specified conduit, while "upstream" refers to the direction opposite that. Thus, for example, the primary flow of working fluid through a gas turbine, which begins as air moving through the compressor and then becomes combustion gases within the combustor and beyond, may be described as beginning at an upstream location toward an upstream or forward end of the compressor and terminating at a downstream location toward a downstream or aft end of the turbine.

Additionally, the term "rotor blade", without further specificity, is a reference to the rotating blades of either the compressor or the turbine, which include both compressor rotor blades and turbine rotor blades. The term "stator blade", without further specificity, is a reference to the stationary blades of either the compressor or the turbine, which include both compressor stator blades and turbine stator blades. The term "blades" will be used herein to refer to either type of blade. Thus, without further specificity, the term "blades" is inclusive to all type of turbine engine blades, including compressor rotor blades, compressor stator blades, turbine rotor blades, and turbine stator blades. Further, the descriptive or standalone term "blade surface" may reference any type of turbine or compressor blade, and may include any or all portions of the blade, including the suction side face, pressure side face, blade tip, blade shroud, platform, root, and shank.

Finally, given the configuration of compressor and turbine about a central common axis, as well as the cylindrical configuration common to many combustor types, terms describing position relative to an axis may be used herein. In this regard, it will be appreciated that the term "radial" refers to movement or position perpendicular to an axis. Related to this, it may be required to describe relative distance from the central axis. In this case, for example, if a first component resides closer to the central axis than a second component, the first component will be described as being either "radially inward" or "inboard" of the second component. If, on the other hand, the first component resides further from the central axis than the second component, the first component will be described herein as being either "radially outward" or "outboard" of the second component. Additionally, as will be appreciated, the term "axial" refers to movement or position parallel to an axis. Finally, the term "circumferential" refers to movement or position around an axis. As mentioned, while these terms may be applied in relation to the common central axis that extends through the compressor and turbine sections of the engine, these terms also may be used in relation to other components or sub-systems of the engine.

By way of background, referring now to the figures, FIGS. 1 through 3 illustrate an exemplary gas turbine in which embodiments of the present application may be used. It will be understood by those skilled in the art that the present invention is not limited to this type of usage. As stated, the present invention may be used in gas turbines, such as the engines used in power generation and airplanes, steam turbine engines, and other types of rotary engines. The examples provided are not meant to be limiting to the type of the turbine engine. FIG. 1 is a schematic representation of a gas turbine 10. In general, gas turbines operate by extracting energy from a pressurized flow of hot gas produced by the combustion of a fuel in a stream of compressed air. As illustrated in FIG. 1, gas turbine 10 may be configured with an axial compressor 11 that is mechanically coupled by a common shaft or rotor to a downstream turbine section or turbine 12, and a combustor 13 positioned between the compressor 11 and the turbine 12. As illustrated in FIG. 1, the gas turbine may be formed about a common central axis 19.

FIG. 2 illustrates a view of an exemplary multi-staged axial compressor 11 that may be used in the gas turbine of FIG. 1. As shown, the compressor 11 may have a plurality of stages, each of which include a row of compressor rotor blades 14 and a row of compressor stator blades 15. Thus, a first stage may include a row of compressor rotor blades 14, which rotate about a central shaft, followed by a row of compressor stator blades 15, which remain stationary during operation. FIG. 3 illustrates a partial view of an exemplary turbine section or turbine 12 that may be used in the gas turbine of FIG. 1. The turbine 12 also may include a plurality of stages. Three exemplary stages are illustrated, but more or less may be present. Each stage may include a plurality of turbine nozzles or stator blades 17, which remain stationary during operation, followed by a plurality of turbine buckets or rotor blades 16, which rotate about the shaft during operation. The turbine stator blades 17 generally are circumferentially spaced one from the other and fixed about the axis of rotation to an outer casing. The turbine rotor blades 16 may be mounted on a turbine wheel or rotor disc (not shown) for rotation about the shaft (not shown). It will be appreciated that the turbine stator blades 17 and turbine rotor blades 16 lie in the hot gas path or working fluid flowpath through the turbine 12. The direction of flow of the combustion gases or working fluid within the working fluid flowpath is indicated by the arrow.

In one example of operation, the rotation of compressor rotor blades 14 within the axial compressor 11 may compress a flow of air. In the combustor 13, energy may be released when the compressed air is mixed with a fuel and ignited. The resulting flow of hot gases or working fluid from the combustor 13 is then directed over the turbine rotor blades 16, which induces the rotation of the turbine rotor blades 16 about the shaft. In this way, the energy of the flow of working fluid is transformed into the mechanical energy of the rotating blades and, given the connection between the rotor blades and the shaft, the rotating shaft. The mechanical energy of the may then be used to drive the rotation of the compressor rotor blades 14, such that the necessary supply of compressed air is produced, and also, for example, a generator to produce electricity.

Figure 4:
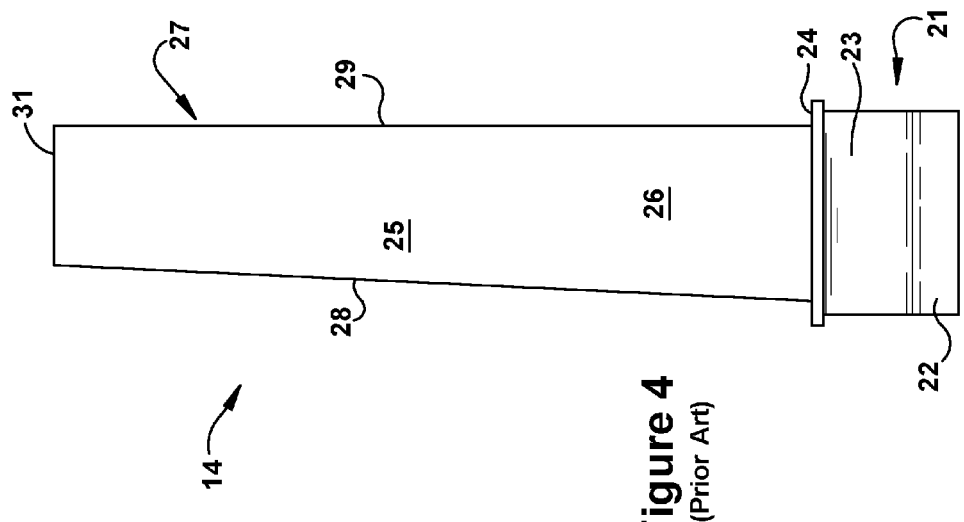
FIG. 4 is a side view of an exemplary turbine blade applicable for inspection according to embodiments of the present invention.

For background purposes, FIG. 4 provides views of an exemplary compressor rotor blade 14 on which aspects of the present invention may be practiced. It will be appreciated that the present invention may be used on other types of blades, within both the turbine and the compressor, and that the exemplary blade of FIG. 4 is provided primarily to illustrate and describe basic blade structure and related subcomponents. As illustrated, the rotor blade 14 may include a root 21 by which it attaches to a rotor disc. For example, the root 21 may include a dovetail 22 configured for mounting in a corresponding dovetail slot in the perimeter of a rotor disc. The root 21 may further include a shank 23 that extends between the dovetail 22 and a platform 24. The platform 24, as shown, is disposed at the junction of the root 21 and an airfoil 25 that extends from it. The airfoil 25 may be configured to define a portion of the inboard boundary of the flowpath through the compressor 11. It will be appreciated that the airfoil 25 is the active component of the rotor blade 14 that interacts with the flow of working fluid through the compressor 11. As stated, while the blade of this example is a compressor rotor blade 14, it will be appreciated that, unless otherwise stated, the present invention also may be applied to other types of blades within the gas turbine 10, including turbine rotor blades 16. It will be understood that the airfoil 25 of the rotor blade 14 may include a concave pressure side face 26 and a circumferentially or laterally opposite convex suction side face 27 extending axially between opposite leading and trailing edges 28, 29 respectively. The side faces 26 and 27 also extend in the radial direction from the platform 24 to an outboard tip 31 of the airfoil 25.

Figure 5:
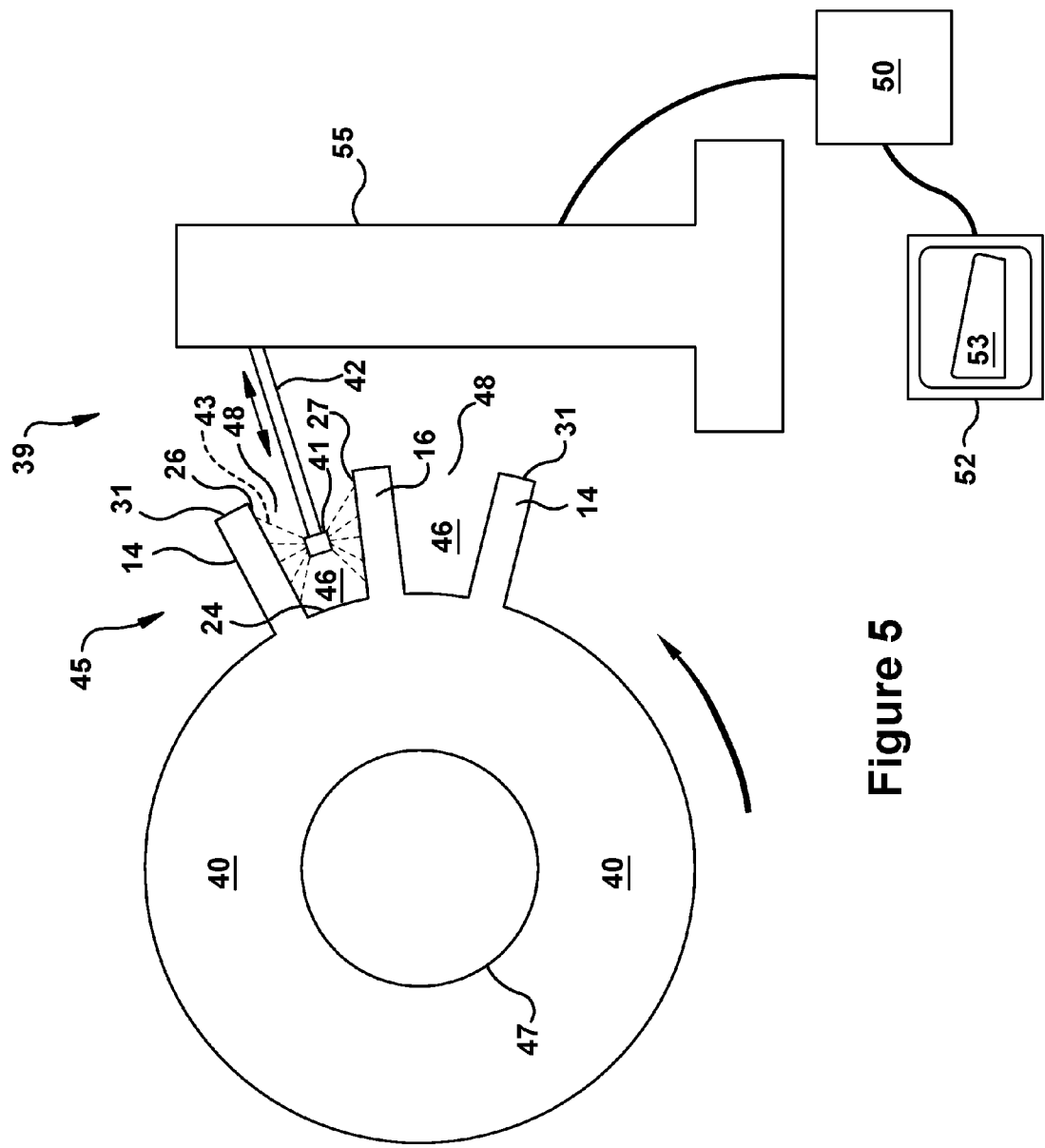
FIG. 5 shows a schematic representation of a system for inspecting blades of a gas turbine according to an exemplary embodiment of the present invention.

In accordance with aspects of the present invention, FIG. 5 shows an illustration of an exemplary inspection system 39 for inspecting surfaces of blades used in gas turbine engines. The system 39 may include a row 45 of rotor blades, only three of which are included in the illustration. For the sake of the example, the row 45 will be discussed as being a row of compressor rotor blades 14, though turbine rotor blades 16 also may be positioned and scanned in the same manner. The row 45 of rotor blades 14 may be in a dissembled condition relative to the turbine engine as a whole, though, the rotor blades 14 within the row 45 may remain in an assembled condition with respect to the rotor disc 40. That is to say, the rotor blades 14 making up the row 45 may remain attached to the rotor disc 40. As schematically indicated, the rotor disc 40, according to preferred embodiments, is engaging by a gear mechanism 47. The gear mechanism 47, per the provided arrow, may controllably rotate the row 45 about a central axis. In this manner, as will be seen, the rotor disc 40 may be rotated in a predetermined manner so to desirably index the rotor blades 14 mounted thereon past the inspection system 39. According to certain embodiments, the rotor disc 40 being rotated is removed or disengaged from the shaft of the gas turbine engine and mounted upon the gear mechanism 47. According to other embodiments, the rotor disc 40 remains mounted on the engine's shaft and is rotated while on the shaft. In such cases, the shaft may be considered part of the gear mechanism 47. As will be appreciated, the gear mechanism 47 may operate by rotating the rotor disc 40 via rotating the shaft on which the rotor disc 40 is mounted.

As will be appreciated, the row 45 includes a gap 46 formed between each pair of neighboring rotor blades 14. Each of these gaps 46 may be circumferentially defined between the pressure side face 26 of one of the neighboring rotor blades 14 and the suction side face 27 of the other. Radially, the gap 46 may be defined between by the abutting platforms 24 of the neighboring rotor blades 14 and a reference plane formed between the outboard tips 31 of the neighboring blades. As will be understood, this reference plane may be designated the outboard mouth 48 of the gap 46. Finally, in regard to axial dimensions, the gap 46 may be described as being defined between a reference plane connecting the leading edges 28 of the neighboring rotor blades 14 and an opposing reference plane connecting the trailing edges of the neighboring rotor blades 14.

The system 39 may include a scanner 41 attached to a movable arm 42. The scanner 41 may be connected to an end of a movable arm or arm 42, as illustrated. The opposing end of the arm 42 may connect to a stationary or movable base 55. According to certain embodiments, the moveable arm 42 is configured as a retracting arm. The system may further include a computer 50 that electronically communicates with the scanner 41 and controls the movement of the arm 42. The movable arm 42 may be configured for controllably moving the scanner 41 between an indexing position and a scanning position. As will be appreciated, the indexing position is one that is outside of the gaps 46 formed between one of the neighboring pairs of the rotor blades 14, whereas the scanning position is a position that is inside one of the gaps 46 formed between the neighboring pairs of rotor blades 14. As will be appreciated, the scanning position is intended for performing the scans, while the indexing position is for removing the scanner 41 and arm 42 assembly from the gaps 46 to so allow relative movement between the assembly and the row of rotor blades 14 without damaging the scanner 41.

In the present configuration, the scanner 41 may project light 43 onto a blade surface within the gap 46 and may detect the projection of the light 43 on the blade surface within the gap 46. The scanner 41 may be configured for scanning the blade surface for surface defects and other characteristics, such as blade surface tears, rips, holes, cracks, pits, creep, and deformities. Preferably, as illustrated, the scanner 41 may include opposed or differently aimed scanners that are configured to scan two different blade surfaces simultaneously. That is to say, the scanner 41 may be configured such that it simultaneously scans the pressure side 26 of one of the neighboring blades 14 and the suction side of the other of the neighboring blade 14 that form the gap 46. Alternatively, the scanner 41 may be rotatably mounted to the movable arm 42.

The light 43 projected by the scanner 41 may be used to profile in detail the scanned surface of the rotor blade 14, which may be used to detection of any flaws or defects that have formed thereon. According to certain embodiments, the light 43 of the scanner 41 may be a form of structured light that changes its shape from an original array of pixels to a distorted array of pixels upon being projected onto the blade surface. In another embodiment, the light 43 projected by the scanner 41 may be laser light. In yet another embodiment, the light 43 projected by the scanner 41 may be visible light.

According to certain preferred embodiments, the scanner 41 may further include a proximity sensor to recognize the position of the scanner 41 with respect to one of the blade surfaces within the gap 46. As will be appreciated, the proximity sensor may aid in positioning the scanner 41 within the gap 46 for accurate surface scans therein. The proximity sensor may comprise any conventional proximity sensor that, for example, emits an electromagnetic field and detects changes to the field resulting from surrounding objects inside the electromagnetic field. The proximity sensor may use sensing circuitry to detect these changes in the emitted electromagnetic field and transmit them to other parts of the system 39. By way of example but not of limitation, the proximity sensor may comprise one or a plurality of proximity sensors including infrared, eddy current, capacitive, photoelectric, or inductive proximity sensors.

The arm 42 may be configured to provide a mechanism for facilitating changes in position of the scanner 41 and to stand as a connecting structure between the scanner 41 and the base 55. The scanner 41 may attach to the arm 42 at any position thereon. According to certain preferred embodiments, the arm 42 may retract and extend, telescopically or otherwise, to predetermined lengths that place the sensor 41 alternatively within the gap 46 and outside of it. The arm 42 may include a desired pitch or angle to allow proper capture of the many types of blade surface that may be scanned during the scanning process. According to certain preferred embodiments, the arm 42 may include one or a plurality of joints along its length for improved maneuverability and flexibility in positioning.

According to preferred embodiments, the indexing of the row of the rotor blades 14 by the gear mechanism 47 may include an intermittent rotation in which rotating periods alternate with stationary periods. In such cases, as will be appreciated, the movable arm 42 may be configured to operate relative to the timing of the intermittent rotation such that the scanner 41 maintains the indexing position during the rotating periods and maintains the scanning position during the stationary periods.

The base 55 may be attached to the arm 42 containing the scanner 41 and may be connected to a computer 50 through a cable or other means such as would allow wireless connection. The base 55 may adjust its position or height to allow for the arm 42 to position the scanner 41 properly along the blade surface. According to certain preferred embodiments, the base 55 may also be able to rotate along different axes as desired.

The computer 50 may be connected to the base 55 via a cable or other means such as would allow wireless connection, and the computer 50 may perform analysis of the input from the scanner 41 that was received from the blade surface. The computer 50 may then calculate the differences between the input from the scanner 41 and a predetermined ideal blade surface. The computer 50 may then compare the differences between the input from the scanner 42 and the predetermined blade surface profile using predetermined thresholds for the differences.

In some embodiments, the computer 50 may ultimately make determinations as to whether the blade surface requires repair, and may recommend which repairs may be needed. According to certain preferred embodiments, the computer 50 may connect to a monitor 52 via a cable and may display an image 53, such as a three-dimensional image, of the scanned blade surface. The computer 50 may mark on each image 53 the areas in need of repair and may generate a report based on predetermined parameters that may describe, for example but not limited to, predicted changes in efficiency, performance, or other selected metrics that may occur after pursuing the recommended repair regimen for the blade surface. According to certain preferred embodiments, the computer 50 may create an output file that may contain inspected images of the blade surface in need of repair. This process may be repeated for every blade surface on the turbine to capture every surface in need of repair into one master output file or in any number of output files.

Figure 6:
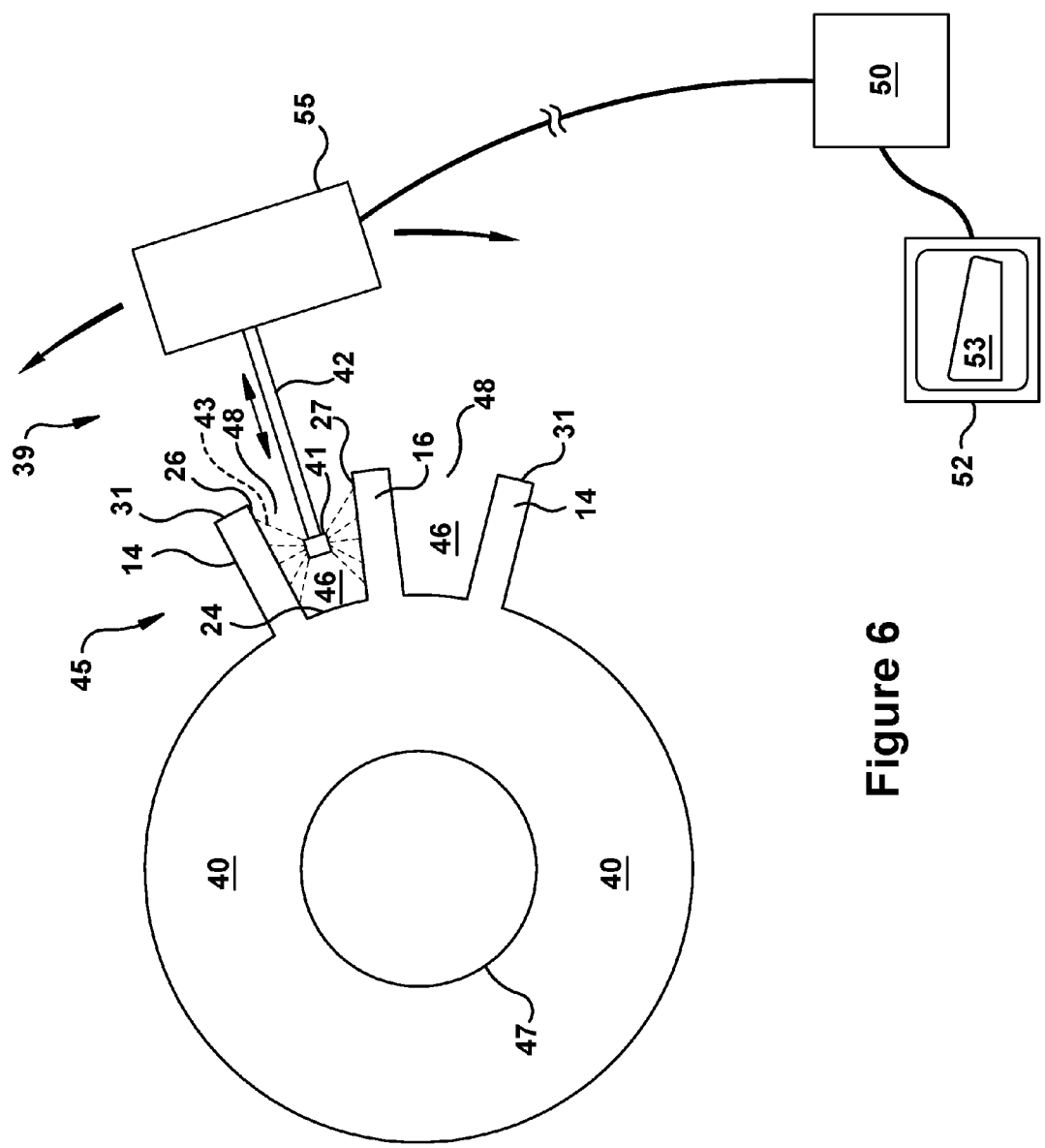
FIG. 6 shows a schematic representation of a system for inspecting blades of a gas turbine according to an alternative embodiment of the present invention.
Figure 7:
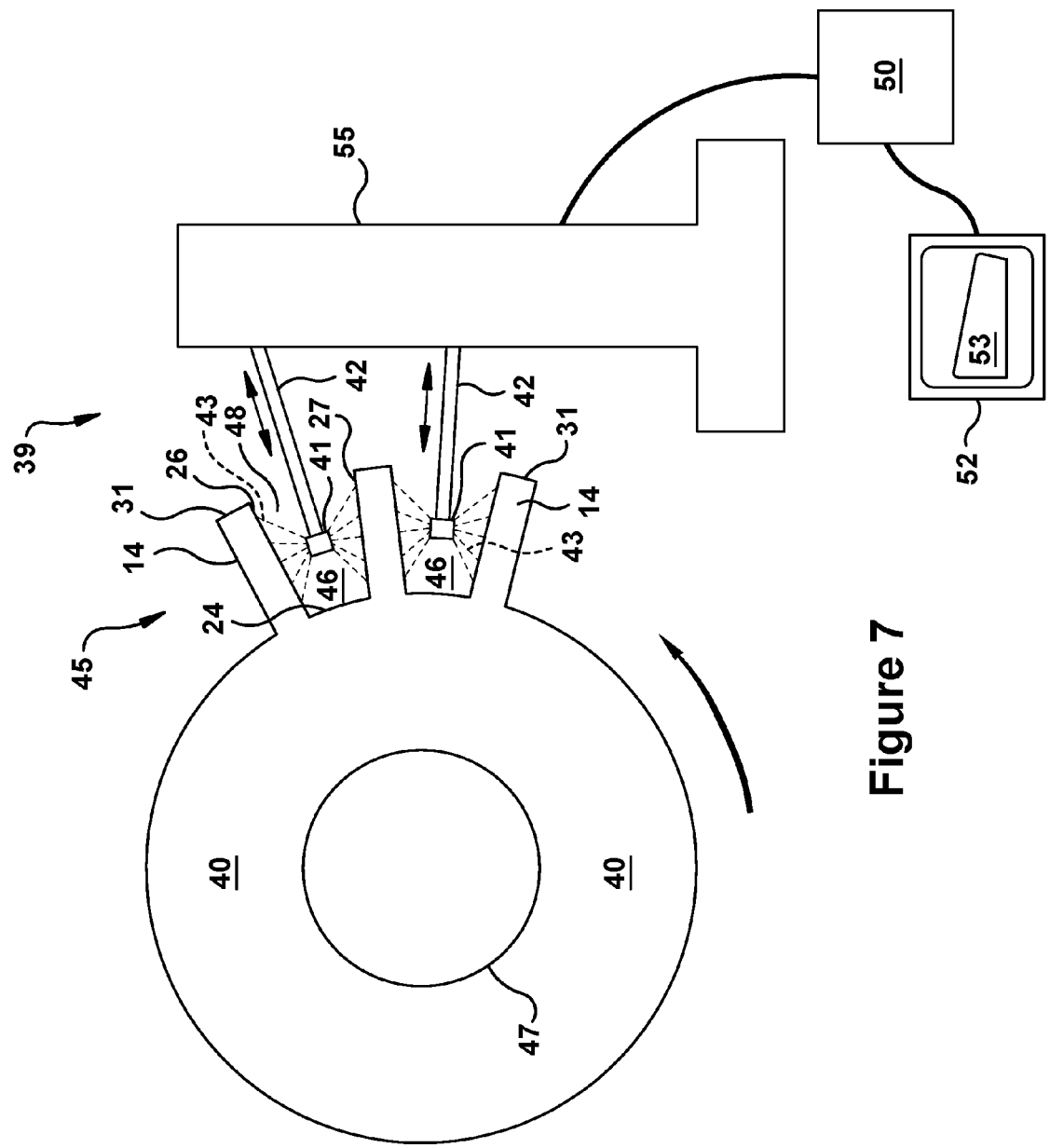
FIG. 7 shows a schematic representation of a system for inspecting blades of a gas turbine according to an alternative embodiment of the present invention.

In an alternative embodiment, as illustrated in FIG. 6, the row 45 of the rotor blades may remain stationary while the device comprises a movable base 55 to which one or a plurality of arms 42 are attached, wherein the base 55 rotates itself around the turbine and scans the surfaces of each blade with the arm 42 and scanner 41 assembly. In another alternative embodiment, as illustrated in FIG. 7, the base 55 may have multiple arms 42 each with include the scanner 41 that perform the same functions to read a plurality of blade surfaces at a plurality of locations or within a plurality of gaps 46 along the row 45 of rotor blades 14.

Figure 8:
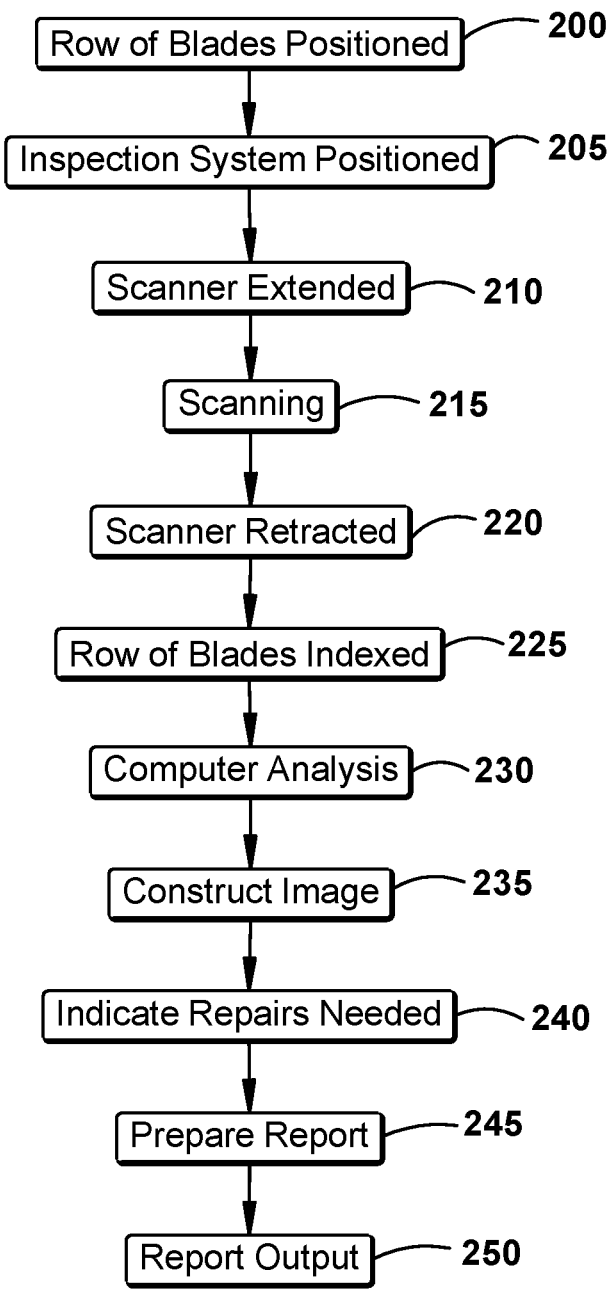
FIG. 8 shows an exemplary method for inspecting blades of a gas turbine according to an embodiment of the present invention.

FIG. 8 is a flow diagram pursuant to an exemplary embodiment of a method for blade surface inspection in accordance with the present invention. The method in FIG. 8 is presented in a specific order as an example only, and as such, the order of various parts of the method can be interchanged, omitted, and/or repeated without deviating from the invention.

At an initial step 200, a row 45 of rotor blades 14 to be inspected may be engaged by the gear mechanism 47, which is configured to rotate the blades 14 at a predetermined rate about a central axis. According to preferred embodiments, the rotor disc 40 holding the rotor blades 14 may be engaged to the gear mechanism 47 and controllably rotated at predetermined timed increments. At a step 205, in accordance with any of the concepts and components already discussed, a device or inspection system 39 assembly may be desirably positioned near the row 45 of rotor blades 14. As already described, the inspection system 39 may include a base 55 and, extending from the base 55, an arm 42 and scanner 41 assembly. Further, the scanner 41 may be positioned at an indexing position, which is one outboard of the outboard mouth 48 of one of the gaps 46 that, as described, is formed between a neighboring pair of rotor blades 14.

At step 210, the arm 42 may be used to extend the scanner 41 to a scanning position, which is one in which the scanner 41 resides inside of the gap 46 formed between the neighboring rotor blades 14. As will be appreciated, in moving from the indexing position to the scanning position, the scanner 46 may move through the outboard mouth 48 of the gap 46, which, as stated, is formed as a reference plane connecting the outboard tips 31 of the airfoils 25 of the neighboring rotor blades 14. At step 215, either while in motion (in moving from the indexing to the scanning position) or once stationary (when the scanning position is reached), the scanner 41 may scan one or more blade surfaces on the neighboring rotor blades 14 for surface characteristics. According to alternative embodiments, the scanner 41 may be moved to a third position to scan other blade surfaces. Once the scanning is complete, at step 220, the scanner 41 may be retracted or be returned to the indexing position. Then, at a step 225, the row 45 of rotor blades 14 may be rotated or indexed such that, on complete, the scanner 41 will reside in the indexing position relative to a different one of the gaps 46 formed between the rotor blades 14. According to alternative embodiments, as will be appreciated, the method may be configured to accommodate the inspection system 39 having multiple arms 42 and scanners 41, as well as configurations in which the row 45 of rotor blades 14 remain stationary and the inspection system rotates about the row 45 of rotor blades 14.

At step 230, the computer 50 may analyze the input received from the scanner 41. The computer 30, for example, may calculate the differences between the input from the scanner, i.e., the scan results, and a predetermined ideal blade surface. The computer 50 may compare the differences between the input from the scanner and the predetermined ideal blade surface to predetermined thresholds. At step 235, the computer 50 may construct and output a three-dimensional image 53 of the blade surface on a monitor 52 operably connected to the computer 50. At step 240, the computer may indicate the areas of the blade surface that have been determined to require repair. At step 245, the computer 50 may then create a report based on predetermined parameters that may describe, for example, predicted changes in efficiency, performance, or other metrics that may occur after pursuing the recommended repair of a blade surface. Finally, at step 250, the computer 50 may output the report to an operator pursuant to conventional means.

As one of ordinary skill in the art will appreciate, the many varying features and configurations described above in relation to the several exemplary embodiments may be further selectively applied to form the other possible embodiments of the present invention. For the sake of brevity and taking into account the abilities of one of ordinary skill in the art, each possible iteration is not herein discussed in detail, though all combinations and possible embodiments embraced by the several claims below are intended to be part of the instant application. In addition, from the above description of several exemplary embodiments of the invention, those skilled in the art will perceive improvements, changes and modifications. Such improvements, changes and modifications within the skill of the art are also intended to be covered by the appended claims.

Further, it should be apparent that the foregoing relates only to the described embodiments of the present application and that numerous changes and modifications may be made herein without departing from the spirit and scope of the application as defined by the following claims and the equivalents thereof.

That which is claimed:

1. A system for inspecting surfaces of rotor blades for a surface characteristic, the system including: an assembly comprising a movable arm and, mounted on the movable arm, a scanner; and
   a row of the rotor blades desirably positioned near the assembly for inspection, the row including at least a plurality of the rotor blades circumferentially spaced about a center axis;
   wherein at least one of the row of the rotor blades and the assembly is moved relative to the other so as to index the row of the rotor blades relative to the assembly;
   a rotor disc having an outer periphery on which the rotor blades of the row of the rotor blades are mounted;
   wherein the each of the rotor blades include an airfoil defined between a concave pressure side face and a laterally opposed convex suction side face, the pressure side face and the suction side face extending axially between opposite leading and trailing edges and radially between an outboard tip and a platform of a root configured for mounting the rotor blade to the rotor disc;
   and wherein the surfaces for inspection comprises as least one of: the pressure side face of the airfoil;
   the suction side, face of the airfoil; the outboard tip of the airfoil; and the platform;
   wherein the row of the rotor blades includes multiple neighboring pairs of the rotor blades; and
   wherein a gap is formed between the airfoils of each of the neighboring pairs of the rotor blades, the gap being defined:
   circumferentially between the pressure side face and the suction side face of the neighboring pairs of the rotor blades;
   radially between the platforms of the neighboring pairs of the rotor blades and a reference, plane connecting the outboard tips of the neighboring pairs of the rotor blades; and
   axially between a reference plane connecting the leading edges of the neighboring pairs of the rotor blades and a reference plane connecting the trailing edges of the neighboring pairs of the rotor blades;
   wherein the movable arm is configured for controllably moving the scanner between an indexing position and a scanning position, wherein: the indexing position comprising a position outside of any of the gaps formed between the neighboring pairs of the rotor blades; and the scanning position comprising a position inside one of the gaps formed between the neighboring pairs of the rotor blades.

2. The system according to claim 1, further comprising a gear mechanism connected to the rotor disc for rotating the row of the rotor blades about the central axis;
   wherein the assembly comprises a stationary base to which the movable arm attaches and the indexing the row of the rotor blades relative to the assembly comprises rotating the rotor disc via the gear mechanism.

3. The system according to claim 2, wherein the outboard tips of the airfoils of each of the neighboring pairs of the rotor blades define an outboard mouth of the gap;

wherein, in moving the scanner between the indexing position to the scanning position, the movable arm passes the scanner through the outboard mouth of the gap; and wherein the gear mechanism comprises a shaft on which the rotor disc is mounted, the shaft comprising a central shaft of a gas turbine engine on which the rotor disc mounts during operation.

4. The system according to claim 2, wherein the surface characteristics include at least one of a tear, rip, hole, crack, pit, creep elongation, and deformity; and the movable arm comprises a retractable arm;

wherein the gear mechanism comprises a shaft on which the rotor disc is mounted, the shaft comprising a separate shaft as a central shaft of a gas turbine engine on which the rotor disc mounts during operation.

5. The system according to claim 2, wherein the scanner further comprises a light source, the light source comprising at least one of: a structured light source, a laser light source, and a visible light source.

6. The system according to claim 5, wherein the scanner further comprises a proximity sensor that includes at least one of an infrared proximity sensor, eddy current proximity sensor, capacitive proximity sensor, photoelectric proximity sensor, and inductive proximity sensor; and wherein the proximity sensor is configured to assist in positioning the scanner in moving between the indexing position and the scanning position.

7. The system according to claim 5, wherein the indexing of the row of the rotor blades by the gear mechanism comprises an intermittent rotation in which rotating periods alternate with stationary periods; and wherein the movable arm is configured to operate relative the intermittent rotation such that the scanner is positioned at the indexing position during the rotating periods and at the scanning position during the stationary periods.

8. The system according to claim 7, wherein the scanner is rotatably mounted on the movable arm; and wherein, upon achieving the scanning position, the scanner is configured to rotate at least once so to adjust an aim of the scanner such that multiple ones of the surfaces of the rotor blades are scanned while the scanner is in the scanning position.

9. The system according to claim 8, wherein the multiple ones of the surfaces that are scanned while the scanner is in the scanning position include the pressure side of a first rotor blade of one of the neighboring pairs of rotor blades and a suction side of a second rotor blade of the one of the neighboring pairs of rotor blades.

10. The system according to claim 7, wherein the scanner comprises a plurality of scanners aimed in a plurality of directions for simultaneously scanning a plurality of the surfaces of the rotor blades with one of the gaps while the scanner is in the scanning position.

11. The system according to claim 10, wherein the multiple ones of the surfaces that are simultaneously scanned while the scanner is in the scanning position include the pressure side of a first rotor blade of one of the neighboring pairs of rotor blades and a suction side of a second rotor blade of the one of the neighboring pairs of rotor blades.

12. The system according to claim 7, further comprising multiple ones of the assembly such that a first assembly includes a first movable arm and a first scanner and a second assembly includes a second movable arm and a second scanner;

wherein the first assembly is configured to simultaneously scan one of the surfaces in a first one of the gaps while the second assembly scans one of the surfaces in a second one of the gaps.

13. The system according to claim 7, further comprising a computer operably connected to the assembly, wherein the computer is configured to:

analyze input regarding the surface characteristics of the surfaces as scanned by the scanner;

calculate differences between the input from the scanner and a reference blade surface; and compare the differences between the input from the scanner and the reference blade surface against predetermined thresholds.

14. The system according to claim 13, wherein the computer is further configured to:

given the comparisons of the differences against the predetermined thresholds, determine repair areas on the surfaces and, for each repair area, repair type;

create a report that includes a predicted performance characteristic related to repairing the repair areas per the repair type that corresponds thereto; and output the report to a system user.

15. The system according to claim 4, wherein the assembly comprises a movable base to which the movable arm attaches and the indexing the row of the rotor blades relative to the assembly comprises moving the movable base about a periphery of the row of rotor blades.

16. A method of inspecting surfaces of rotor blades mounted on a rotor disc for a surface characteristic, the method comprising the steps of:

desirably positioning an assembly that includes a scanner mounted on a movable arm near the rotor blades;

rotating the rotor disc so to index the rotor blades relative to the assembly;

controllably moving the scanner via the moveable arm between an indexing position and a scanning position, wherein:

the indexing position comprises a position outside of any of the gaps formed between the neighboring pairs of the rotor blades; and the scanning position comprises a position inside one of the gaps formed between the neighboring pairs of the rotor blades; and scanning the surfaces of the rotor blades when the scanner maintains the indexing position.

17. The method according to claim 16, wherein each of the rotor blades include an airfoil defined between a concave pressure side face and a laterally opposed convex suction side face, the pressure side face and the suction side face extending axially between opposite leading and trailing edges and radially between an outboard tip and a platform of a root configured for mounting the rotor blade to the rotor disc; and wherein the surfaces for inspection comprises as least one of: the pressure side face of the airfoil;

the suction side face of the airfoil; the outboard tip of the airfoil; and the platform.

18. The method according to claim 17, wherein the rotor blades include multiple neighboring pairs of the rotor blades; and wherein a gap is formed between the airfoils of each of the neighboring pairs of the rotor blades, the gap being defined:

circumferentially between the pressure side face and the suction side face of the neighboring pairs of the rotor blades;

radially between the platforms of the neighboring pairs of the rotor blades and a reference plane connecting the outboard tips of the neighboring pairs of the rotor blades; and axially between a reference plane connecting the leading edges of the neighboring pairs of the rotor blades and a reference plane connecting the trailing edges of the neighboring pairs of the rotor blades; and wherein, in controllably moving the scanner between the indexing position and the scanning position, the movable arm passes the scanner through the reference plane connecting the outboard tips of the neighboring pairs of the rotor blades.

19. The method according to claim 18, wherein the scanner further comprises a structured light source;

wherein the rotating the rotor disc comprises an intermittent rotation in which rotating periods alternative with stationary periods; and wherein the controllably moving the scanner via the moveable arm between the indexing position and the scanning position includes: timing the movement pursuant to the intermittent rotation such that the scanner comprises the indexing position during the rotating periods and the scanning position during the stationary periods.

* * * * *